(12) United States Patent
Ress-Löschke et al.

(10) Patent No.: US 6,869,783 B1
(45) Date of Patent: Mar. 22, 2005

(54) METHOD FOR PRODUCING CHIRAL CARBOXYLIC ACIDS FROM NITRILES WITH THE ASSISTANCE OF A NITRILASE OR MICROORGANISMS WHICH CONTAIN A GENE FOR THE NITRILASE

(75) Inventors: Marion Ress-Löschke, Dossenheim (DE); Thomas Friedrich, Darmstadt (DE); Bernhard Hauer, Fussgönheim (DE); Ralf Mattes, Stuttgart (DE); Dirk Engels, Walddorfhäslach (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/806,876

(22) PCT Filed: Oct. 13, 1999

(86) PCT No.: PCT/EP99/07679

§ 371 (c)(1),
(2), (4) Date: Apr. 5, 2001

(87) PCT Pub. No.: WO00/23577

PCT Pub. Date: Apr. 27, 2000

(30) Foreign Application Priority Data

Oct. 19, 1998 (DE) .......................................... 198 48 129

(51) Int. Cl.[7] .................................................. C12P 7/62
(52) U.S. Cl. ...................... 435/135; 435/132; 435/136; 435/183; 435/227; 435/252.3; 435/320.1; 536/23.2
(58) Field of Search ................................ 435/132, 135, 435/136, 183, 227, 252.3, 320.1; 536/23.2

(56) References Cited

U.S. PATENT DOCUMENTS

| 5,283,193 A | 2/1994 | Yamamoto |
| 5,296,373 A | 3/1994 | Endo |

FOREIGN PATENT DOCUMENTS

| EP | 332 379 | 9/1989 |
| EP | 348 901 | 1/1990 |
| EP | 349 901 | 1/1990 |
| EP | 449 648 | 10/1991 |
| EP | 473 328 | 3/1992 |
| EP | 527 553 | 2/1993 |
| EP | 610 048 | 8/1994 |
| EP | 610 049 | 8/1994 |
| EP | 666 320 | 8/1995 |
| EP | 719 862 | 7/1996 |
| WO | 92/05275 | 4/1992 |
| WO | WO97/32030 | 9/1997 |
| WO | 97/32030 | 9/1997 |

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief Bioinform. Mar. 2001, vol. 2(1), pp. 19–29.*
Kobayashi et al. Accession D13419.*
Kobayashi et al. Accession A47181.*
Kobayashi et al. Nitrilase in biosynthesis of the plant hormone indole–3–acetic acid from indole–3–acetonitrile: cloning of the Alcaligenes gene and site–directed mutagenesis of cysteine residues. Proc. Natl. Acad. Sci. U.S.A. 90 (1), 247–251 (1993)).*
NucAcidsRes,vol.20,May 11, 1992,Wada et al.,211–2118.
J.Biochem,1990,194, 765–772,Nagasawa et al.
Mol.Mic.1996,21,1037–1047,Volff et al.
J.Mol.Bio, vol.243,No. 4, Nov. 1994,Egan etal.821–829.
Proc.Natl.Acad.Sci,vol.90,247–251,1/93,Kobayashi etal.

* cited by examiner

*Primary Examiner*—Ponnathapu Achutamurthy
*Assistant Examiner*—Christian L Fronda
(74) *Attorney, Agent, or Firm*—Keil & Weinkauf

(57) ABSTRACT

The invention relates to nucleic acid sequences which code for a polypeptide having nitrilase activity, to nucleic acid constructs comprising the nucleic acid sequences, and to vectors comprising the nucleic acid sequences or the nucleic acid constructs. The invention further relates to amino acid sequences which are encoded by the nucleic acid sequences, and to microorganisms comprising the nucleic acid sequences, the nucleic acid constructs or vectors comprising the nucleic acid sequences or the nucleic acid constructs.

The invention additionally relates to a process for preparing chiral carboxylic acids from the racemic nitriles.

15 Claims, 6 Drawing Sheets

METHOD FOR PRODUCING CHIRAL CARBOXYLIC ACIDS FROM NITRILES WITH THE ASSISTANCE OF A NITRILASE OR MICROOGANISMS WHICH CONTAIN A GENE FOR THE NITRILASE

The invention relates to nucleic acid sequences which code for a polypeptide having nitrilase activity, to nucleic acid constructs comprising the nucleic acid sequences, and to vectors comprising the nucleic acid sequences or the nucleic acid constructs. The invention further relates to amino acid sequences which are encoded by the nucleic acid sequences, and to microorganisms comprising the nucleic acid sequences, the nucleic acid constructs or vectors comprising the nucleic acid sequences or the nucleic acid constructs.

The invention additionally relates to a process for preparing chiral carboxylic acids from the racemic nitrites.

Chiral carboxylic acids are compounds in demand for organic chemical synthesis. They are starting materials for a large number of pharmaceutical active ingredients or active ingredients for crop protection. Chiral carboxylic acids can be used for classical racemate resolution via diastereomeric salts. Thus, R—(−)— or S—(−)-mandelic [sic] acid is employed, for example, for racemate resolution of racemic amines. R—(−)-Mandelic acid is additionally used as intermediate for synthesizing semisynthetic antibiotics and a large number of agricultural products.

Various different synthetic routes to chiral carboxylic acids are disclosed in the literature. Thus, for example, optically active amino acids are obtained industrially by fermentation processes. These entail the disadvantage that a specific process must be developed for each amino acid. This is why chemical or enzymatic processes are used in order to be able to prepare a maximally wide range of different compounds. A disadvantage of chemical processes is that the stereocenter usually has to be constructed in complicated, multistage, not widely applicable synthesis [sic].

The enzymatic synthesis of chiral carboxylic acids are [sic] to be found in a number of patents or patent applications. WO92/05275 describes the synthesis of enantiomeric α-hydroxy-α-alkyl- or α-alkylcarboxylic acids in the presence of biological materials. EP-B-0 348 901 claims a process for preparing optically active α-substituted organic acids using microorganisms of the genera Alcaligenes, Pseudomonas, Rhodopseudomonas, Corynebacterium sp. strain KO-2-4, Acinetobacter, Bacillus, Mycobacterium, Rhodococcus and Candida. The preparation of L-α-amino acids using microorganisms is claimed in EP-B-0 332 379.

The preparation of α-hydroxycarboxylic acids, specifically the preparation of optically active lactic acid or mandelic acid, using various microorganisms, such as microorganisms of the genera Alcaligenes, Aureobacterium, Pseudomonas, Rhodopseudomonas, Corynebacterium, Acinetobacter, Caseobacter, Bacillus, Mycobacterium, Rhodococcus, Brevibacterium, Nocardia, Variovorax, Arthrobacter and Candida or using enzymes is described in the patents EP-A-0 348 901 or its US equivalent U.S. Pat. No. 5,283,193, EP-A-0 449 648, EP-B-0 473 328, EP-B-0 527 553 or its US equivalent U.S. Pat. No. 5,296,373, EP-A-0 610 048, EP-A-0 610 049, EP-A 0 666 320 or WO97/32030.

The disadvantages of these processes is that they often lead to products with only low optical purity and/or that they proceed with only low space-time yields. This leads to economically unattractive processes. Even attempts to increase the productivity by adding substances such as sulfite, disulfite, dithionite, hypophosphite or phosphite (see EP-A 0 486 289) or by use of microorganisms having an increased resistance to α-hydroxy nitrites (see WO97/32030) lead to a negligible increase in productivity.

It is an object of the present invention to develop an easy, cost-effective, widely applicable process for preparing optically active chiral carboxylic acids which does not have the abovementioned disadvantages.

We have found that this object is achieved by the process according to the invention for preparing chiral carboxylic acids of the general formula I

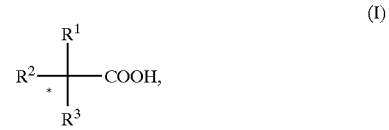

which comprises converting racemic nitrites of the general formula II

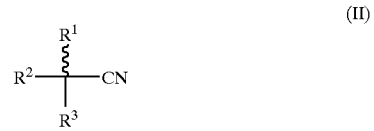

in the presence of an amino acid sequence which is encoded by a nucleic acid sequence selected from the group of
a) a nucleic acid sequence having the sequence depicted in SEQ ID NO: 1,
b) nucleic acid sequences which are derived from the nucleic acid sequence depicted in SEQ ID NO: 1 as a result of the degeneracy of the genetic code,
c) derivatives of the nucleic acid sequence depicted in SEQ ID NO: 1, which code for polypeptides having the amino acid sequences depicted in SEQ ID NO: 2 and have at least 80% homology at the amino acid level, with negligible reduction in the enzymatic action of the polypeptides, or a growing, dormant or disrupted microorganism which comprises either a nucleic acid sequence from the abovementioned group or a nucleic acid construct which links a nucleic acid from said group to one or more regulatory signals, and where at least 25 mmol of nitrile are converted per h and per mg of protein or 25 mmol of nitrile are converted per h and per g of dry weight into the chiral carboxylic acids, where the substituents and variables in the formulae I and II have the following meanings:
an optically active center
$R^1$, $R^2$, $R^3$ independently of one another hydrogen, substituted or unsubstituted, branched or unbranched $C_1$–$C_1$-alkyl, $C_2$–$C_{10}$-alkenyl, substituted or unsubstituted aryl, hetaryl, $OR^4$ or $NR^4R^5$ and where the radicals $R^1$, $R^2$ and $R^3$ are always different,
$R^4$ hydrogen, substituted or unsubstituted, branched or unbranched $C_1$–$C_{10}$-alkyl, $C_2$–$C_{10}$-alkenyl, $C_1$–$C_{10}$-alkylcarbonyl, $C_2$–$C_{10}$-alkenylcarbonyl, aryl, arylcarbonyl, hetaryl or hetarylcarbonyl,
$R^5$ hydrogen, substituted or unsubstituted, branched or unbranched $C_1$–$C_{10}$-alkyl, $C_2$–$C_{10}$-alkenyl, aryl or hetaryl.
$R^1$, $R^2$, $R^3$ in the compounds of the formulae I and II are, independently of one another, hydrogen, substituted or unsubstituted, branched or unbranched $C_1$–$C_{10}$-alkyl, $C_2$–$C_{10}$-alkenyl, substituted or unsubstituted aryl, hetaryl, $OR^4$ or $NR^4R^5$ and where the radicals $R^1$, $R^2$ and $R^3$ are always different.

DETAILED DESCRIPTION OF THE INVENTION

Figure 1:
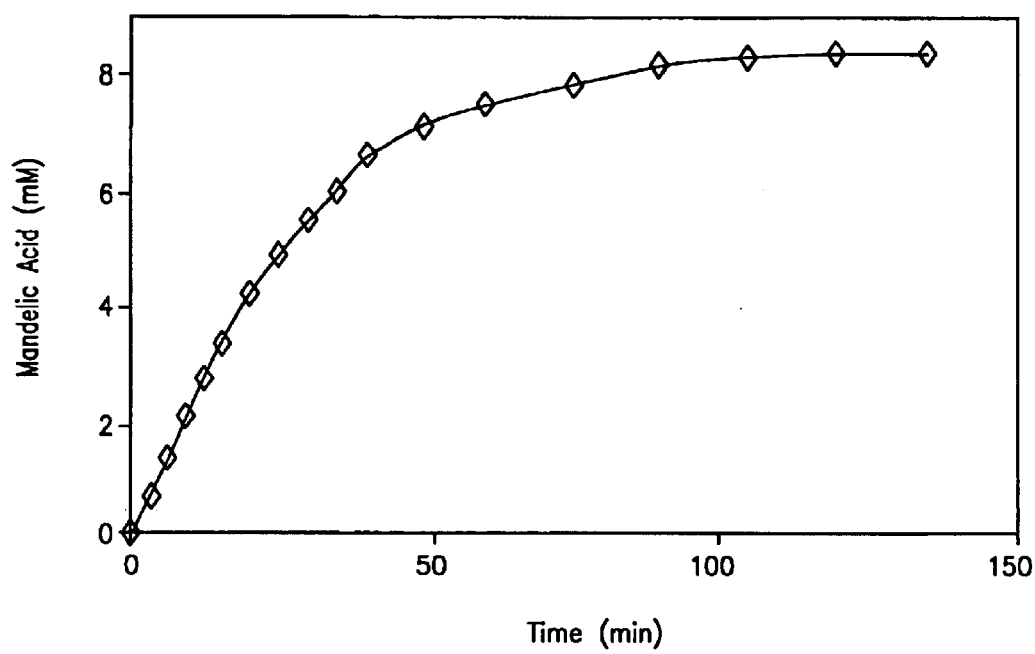
FIG. 1 depicts the conversion of mandelonitrile into mandelic acid using Alcaligenes faecalis 1605 cells, in a batch, as a function of time.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are branched or unbranched $C_2$–$C_{10}$-alkenyl chains such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl or decenyl. Ethenyl, propenyl, butenyl or pentenyl are preferred.

Aryl radicals which may be mentioned are substituted and unsubstituted aryl radicals which contain 6 to 20 carbon atoms in the ring or ring system. The latter may comprise aromatic rings which are fused together or aromatic rings linked by alkyl, alkylcarbonyl, alkenyl or alkenylcarbonyl chains, carbonyl, oxygen or nitrogen. The aryl radicals may, where appropriate, also be linked via $C_1$–$C_{10}$-alkyl, $C_3$–$C_8$-alkenyl, $C_3$–$C_6$-alkynyl or $C_3$–$C_8$-cycloalkyl chain to the basic framework. Phenyl or naphthyl are preferred.

Hetaryl [lacuna] which may be mentioned are substituted or unsubstituted, single or fused aromatic ring systems with one or more heteroaromatic 3- to 7-membered rings which may contain one or more heteroatoms such as N, O or S and may, where appropriate, be linked via a $C_1$–$C_{10}$-alkyl, $C_3$–$C_8$-alkenyl or $C_3$–$C_8$-cycloalkyl chain to the basic framework. Examples of hetaryl radicals of this type are pyrazole, imidazole, oxazole, isooxazole [sic], thiazole, triazole, pyridine, quinoline, isoquinoline, acridine, pyrimidine, pyridazine, pyrazine, phenazine, purine or pteridine. The hetaryl radicals may be linked to the basic framework via the hetero atoms or via the various carbon atoms in the ring or ring system or via the substituents. Pyridine, imidazole, pyrimidine, purine, pyrazine or quinoline are preferred.

Suitable substituents for said $R^1$, $R^2$ or $R^3$ radicals are, for example, one or more substituents such as halogen such as fluorine, chlorine or bromine, thio [sic], nitro, amino, hydroxyl, alkyl, alkoxy, alkenyl, alkenyloxy, alkynyl or other aromatic or other saturated or unsaturated nonaromatic rings or ring systems. Preference is given to alkyl radicals such as $C_1$–$C_6$-alkyl such as methyl, ethyl, propyl or butyl, aryl such as phenyl, halogen such as chlorine, fluorine or bromine, hydroxyl or amino.

$R^4$ in the $OR^4$ or $NR^4R^5$ radicals is hydrogen, substituted or unsubstituted, branched or unbranched $C_1$–$C_{10}$-alkyl, $C_2$–$C_{10}$-alkenyl, $C_1$–$C_{10}$-alkylcarbonyl, $C_2$–$C_{10}$-alkenylcarbonyl, aryl, arylcarbonyl, hetaryl or hetarylcarbonyl.

Alkyl radicals which may be mentioned are substituted or unsubstituted, branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl or i-butyl are preferred.

Alkenyl radicals which may be mentioned are branched or unbranched $C_2$–$C_{10}$-alkenyl chains such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-Methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl or decenyl. Ethenyl, propenyl, butenyl or pentenyl are preferred.

Alkylcarbonyl radicals which may be mentioned are substituted or unsubstituted, branched or unbranched $C_1$–$C_{10}$-alkylcarbonyl chains such as, for example, methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, n-hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl, 1-ethyl-2-methylpropylcarbonyl, n-heptylcarbonyl, n-octylcarbonyl, n-nonylcarbonyl or n-decylcarbonyl. Methylcarbonyl, ethylcarbonyl, n-propylcarbonyl, n-butylcarbonyl, i-propylcarbonyl or i-butylcarbonyl are preferred.

Alkenylcarbonyl radicals which may be mentioned are branched or unbranched $C_2$–$C_{10}$-alkenylcarbonyl chains such as, for example, ethenylcarbonyl, propenylcarbonyl, 1-butenylcarbonyl, 2-butenylcarbonyl, 3-butenylcarbonyl, 2-methylpropenylcarbonyl, 1-pentenylcarbonyl, 2-pentenylcarbonyl, 3-pentenylcarbonyl, 4-pentenylcarbonyl, 1-methyl-1-butenylcarbonyl, 2-methyl-1-butenylcarbonyl, 3-methyl-1-butenylcarbonyl, 1-methyl-2-butenylcarbonyl, 2-methyl-2-butenylcarbonyl, 3-methyl-2-butenylcarbonyl, 1-methyl-3-butenylcarbonyl, 2-methyl-3-butenylcarbonyl, 3-methyl-3-butenylcarbonyl, 1,1-dimethyl-2-propenylcarbonyl, 1,2-dimethyl-1-propenylcarbonyl, 1,2-dimethyl-2-propenylcarbonyl, 1-ethyl-1-propenylcarbonyl, 1-ethyl-2-propenylcarbonyl, 1-hexenylcarbonyl, 2-hexenylcarbonyl, 3-hexenylcarbonyl, 4-hexenylcarbonyl, 5-hexenylcarbonyl, 1-methyl-1-pentenylcarbonyl, 2-methyl-1-pentenylcarbonyl, 3-methyl-1-pentenylcarbonyl, 4-methyl-1-pentenylcarbonyl, 1-methyl-2-pentenylcarbonyl, 2-methyl-2-pentenylcarbonyl, 3-methyl-2-pentenylcarbonyl, 4-methyl-2-pentenylcarbonyl, 1-methyl-3-pentenylcarbonyl, 2-methyl-3-pentenylcarbonyl, 3-methyl-3-pentenylcarbonyl, 4-methyl-3-pentenylcarbonyl, 1-methyl-4-pentenylcarbonyl, 2-methyl-4-pentenylcarbonyl, 3-methyl-4-pentenylcarbonyl, 4-methyl-4-pentenylcarbonyl, 1,1-dimethyl-2-butenylcarbonyl, 1,1-dimethyl-3-butenylcarbonyl, 1,2-dimethyl-1-butenylcarbonyl, 1,2-dimethyl-2-butenylcarbonyl, 1,2-dimethyl-3-butenylcarbonyl, 1,3-dimethyl-1-butenylcarbonyl, 1,3-dimethyl-2-butenylcarbonyl, 1,3-dimethyl-3-butenylcarbonyl, 2,2-dimethyl-3-butenylcarbonyl, 2,3-dimethyl-1-butenylcarbonyl, 2,3-dimethyl-2-butenylcarbonyl, 2,3-dimethyl-3-butenylcarbonyl, 3,3-dimethyl-1-butenylcarbonyl, 3,3-dimethyl-2-butenylcarbonyl, 1-ethyl-1-butenylcarbonyl, 1-ethyl-2-butenylcarbonyl, 1-ethyl-3-butenylcarbonyl, 2-ethyl-1-butenylcarbonyl, 2-ethyl-2-butenylcarbonyl, 2-ethyl-3-butenylcarbonyl, 1,1,2-trimethyl-2-propenylcarbonyl, 1-ethyl-1-methyl-2-propenylcarbonyl, 1-ethyl-2-methyl-1-propenylcarbonyl, 1-ethyl-2-methyl-2-propenylcarbonyl, 1-heptenylcarbonyl, 2-heptenylcarbonyl, 3-heptenylcarbonyl, 4-heptenylcarbonyl, 5-heptenylcarbonyl, 6-heptenylcarbonyl, 1-octenylcarbonyl, 2-octenylcarbonyl, 3-octenylcarbonyl, 4-octenylcarbonyl, 5-octenylcarbonyl, 6-octenylcarbonyl, 7-octenylcarbonyl, nonenylcarbonyl or decenylcarbonyl. Ethenylcarbonyl, propenylcarbonyl, butenylcarbonyl or pentenylcarbonyl are preferred.

Aryl radicals which may be mentioned are substituted and unsubstituted aryl radicals which contain 6 to 20 carbon atoms in the ring or ring system. The latter may comprise aromatic rings which are fused together or aromatic rings which are linked via alkyl, alkylcarbonyl, alkenyl or alkenylcarbonyl chains, carbonyl, oxygen or nitrogen. The aryl radicals may, where appropriate, also be linked via a $C_1$–$C_{10}$-alkyl, $C_3$–$C_8$-alkenyl, $C_3$–$C_6$-alkynyl or $C_3$–$C_8$-cycloalkyl chain to the basic framework. Phenyl or naphthyl are preferred.

Arylcarbonyl radicals which may be mentioned are substituted and unsubstituted arylcarbonyl radicals which contain 6 to 20 carbon atoms in the ring or ring system. The latter may comprise aromatic rings which are fused together or aromatic rings which are linked via alkyl, alkylcarbonyl, alkenyl or alkenylcarbonyl chains, carbonyl, oxygen or nitrogen. Phenylcarbonyl or naphthylcarbonyl are preferred.

Hetaryl [lacuna] which may be mentioned are substituted or unsubstituted, single or fused aromatic ring systems with one or more heteroaromatic 3- to 7-membered rings which may contain one or more heteroatoms such as N, O or S and may, where appropriate, be linked via a $C_1$–$C_{10}$-alkyl, $C_3$–$C_8$-alkenyl or $C_3$–$C_8$-cycloalkyl chain to the basic framework. Examples of hetaryl radicals of this type are pyrazole, imidazole, oxazole, isooxazole [sic], thiazole, triazole, pyridine, quinoline, isoquinoline, acridine, pyrimidine, pyridazine, pyrazine, phenazine, purine or pteridine. The hetaryl radicals may be linked to the basic framework via the heteroatoms or via the various carbon atoms in the ring or ring system or via the substituents. Hetarylcarbonyl radicals mean heteroaromatic radicals which are linked via a carbonyl radical to the basic framework. Pyridine, imidazole, pyrimidine, purine, pyrazine or quinoline are preferred.

Suitable substituents for said $R^4$ radicals are, for example, one or more substituents such as halogen such as fluorine, chlorine or bromine, thio [sic], nitro, amino, hydroxyl, alkyl, alkoxy, alkenyl, alkenyloxy, alkynyl or other aromatic or other saturated or unsaturated nonaromatic rings or ring systems. Preference is given to alkyl radicals such as $C_1$–$C_6$- alkyl such as methyl, ethyl, propyl or butyl, halogen such as chlorine, fluorine or bromine, hydroxyl or amino.

The $R^4$ radical is preferably hydrogen.

$R^5$ in the $NR^4R^5$ radical is hydrogen, substituted or unsubstituted, branched or unbranched $C_1$–$C_{10}$-alkyl, $C_2$–$C_{10}$-alkenyl, aryl or hetaryl, where the alkyl, alkenyl, aryl and hetaryl radicals have the abovementioned meanings. Preference is given to hydrogen or $C_1$–$C_{10}$-alkyl such as methyl, ethyl or propyl.

Suitable substituents for said $R^5$ radicals are, for example, one or more substituents such as halogen such as fluorine, chlorine or bromine, thio [sic], nitro, amino, hydroxyl, alkyl, alkoxy, alkenyl, alkenyloxy, alkynyl or other aromatic or other saturated or unsaturated nonaromatic rings or ring systems. Preference is given to alkyl radicals such as $C_1$–$C_6$-alkyl such as methyl, ethyl, propyl or butyl, aryl such as phenyl, halogen such as chlorine, fluorine or bromine, hydroxyl or amino.

It is further possible for two adjacent $R^4$ or $R^5$ substituents together to form another substituted or unsubstituted aromatic, saturated or partially saturated ring with 5 to 6 atoms in the ring which may contain one or more heteroatoms such as O, N or S.

It is advantageous for one of the $R^1$, $R^2$ or $R^3$ substituents in the formulae I and II to be aryl, such as phenyl. It is further preferred for one of the $R_1$, $R^2$ or $R^3$ substituents in the formulae I and II to be hydroxyl and one to be hydrogen or methyl.

The process according to the invention is advantageously carried out at a pH of from 4 to 11, preferably from 4 to 9.

It is further advantageous to use from 0.01 to 10% by weight of nitrile or 0.01 to 10% by weight of a corresponding aldehyde or ketone and 0.01 to 10% by weight of hydrocyanic acid in the process. The process is advantageously carried out with an excess of hydrocyanic acid. In some circumstances, this leads to hydrocyanic acid contents which are higher than those stated. Various amounts of nitrile can be used in the reaction, depending on the nitrile. The smallest amounts (=amounts between 0.01 to [sic] 5% by weight) of nitrile are advantageously used for nitriles (cyanohydrins) which are in equilibrium with the corresponding aldehydes and hydrocyanic acid. Since the aldehyde is usually toxic for the microorganisms or enzymes. Volatile nitriles are likewise advantageously employed in amounts between 0.01 to [sic] 5% by weight. The reaction is retarded with larger amounts of cyanohydrin or nitrile. In the case of nitrites which have only low or virtually no solvent properties, or nitriles which dissolve in only very small amounts in aqueous medium, it is possible and advantageous to employ larger amounts than those stated above. To increase the conversion and the yield, the reaction is advantageously carried out with controlled addition of the racemic nitrile. The product can be isolated after the end of the reaction or else be removed continuously in a bypass.

The abovementioned appropriate aldehydes or ketones mean compounds which form the nitrile after reaction between the aldehyde or ketone and hydrocyanic acid, where appropriate with acid catalysis. The reaction between aldehyde and hydrocyanic acid results in cyanohydrins which have the advantage that they are in equilibrium with aldehyde and hydrocyanic acid. The setting up of an equilibrium with the cyanohydrin means that it is possible with an enzyme which converts only one enantiomer of the nitrile nevertheless to obtain a yield of 100% of theory because the racemic nitrile is continually replenished. With all other nitrites, the nitrile not converted by the enzyme (="wrong"

or other enantiomer) is advantageously racemized by a chemical reaction and returned to the process in order to be able to reach a theoretical yield of 100%, or is discarded or purified and chemically hydrolyzed with retention of the stereocenter.

The process according to the invention is advantageously carried out at a temperature between 0° C. to [sic] 80° C., preferably between 10° C. to [sic] 60° C., particularly preferably between 15° C. to [sic] 50° C.

Racemic nitriles in the process according to the invention mean nitriles which consist of a 50:50 mixture of the two enantiomers or of any other mixture with enrichment of one of the two enantiomers in the mixture.

Chiral carboxylic acids in the process according to the invention mean those showing an enantiomeric enrichment. The process preferably results in enantiomeric purities of at least 90% ee, preferably of min. 95% ee, particularly preferably of min. 98% ee, very particularly preferably min. 99% ee.

The process according to the invention makes it possible to convert a large number of racemic nitrites into the chiral carboxylic acids. It is possible in the process to convert at least 25 mmol of nitrile/h×mg of protein or at least 25 mmol of nitrile/h×g dry weight of the microorganisms, preferably at least 30 mmol of nitrile/h×mg of protein or at least 30 mmol of nitrile/h×g dry weight, particularly preferably at least 40 mmol of nitrile/h×mg of protein or at least 40 mmol of nitrile/h×g dry weight, very particularly preferably at least 50 mmol of nitrile/h×mg of protein or at least 50 mmol of nitrile/h×g dry weight.

It is possible to use growing cells which comprise the nucleic acids, nucleic acid constructs or vectors according to the invention for the process according to the invention. Dormant or disrupted cells can also be used. Disrupted cells mean, for example, cells which have been made permeable by a treatment with, for example, solvents, or cells which have been disintegrated by an enzyme treatment, by a mechanical treatment (e.g. French press or ultrasound) or by any other method. The crude exracts obtained in this way are suitable and advantageous for the process according to the invention. Purified or partially purified enzymes can also be used for the process. Immobilized microorganisms or enzymes are likewise suitable and can advantageously be used in the reaction.

The chiral carboxylic acids prepared in the process according to the invention can advantageously be isolated from the aqueous reaction solution by extraction or crystallization or by extraction and crystallization. For this purpose, the aqueous reaction solution is acidified with an acid such as a mineral acid (e.g. HCl or $H_2SO_4$) or an organic acid, advantageously to pH values below 2, and then extracted with an organic solvent. The extraction can be repeated several times to increase the yield. Organic solvents which can be used are in principle all solvents which show a phase boundary with water, where appropriate after addition of salts. Advantageous solvents are solvents such as toluene, benzene, hexane, methyl tert-butyl ether or ethyl acetate.

After concentration of the organic phase, the products can usually be isolated in good chemical purities, meaning a chemical purity of greater than 90%. After extraction, the organic phase with the product can, however, also be only partly concentrated, and the product can be crystallized. For this purpose, the solution is advantageously cooled to a temperature of from 0° C. to 10° C. The crystallization can also take place directly from the organic solution. The crystallized product can be taken up again in the same or a different solvent for renewed crystallization and be crystallized once again. The subsequent crystallization at least once may, depending on the position of the eutectic composition, further increase the enantiomeric purity of the product.

The chiral carboxylic acids can, however, also be crystallized out of the aqueous reaction solution immediately after acidification with an acid to a pH advantageously below 2. This advantageously entails the aqueous solution being concentrated by heating to reduce its volume by 10 to 90%, preferably 20 to 80%, particularly preferably 30 to 70%. The crystallization is preferably carried out with cooling. Temperatures between 0° C. to [sic] 10° C. are preferred for the crystallization. Direct crystallization from the aqueous solution is preferred for reasons of cost. It is likewise preferred to work up the chiral carboxylic acids via extraction and, where appropriate, subsequent crystallization.

With these preferred types of workup, the product of the process a 25 according to the invention can be isolated in yields of from 60 to 10%, preferably from 80 to 100%, particularly preferably from 90 to 100%, based on the nitrile employed for the reaction. The isolated product has a high chemical purity of >90%, preferably >95%, particularly preferably >98%. In addition, the product [sic] have high enantiomeric purity, which may be increased further by crystallization.

The products obtained in this way are suitable as starting material for organic syntheses to prepare drugs or agrochemicals or for racemate resolution.

The invention further relates to an isolated nucleic acid sequence which codes for a polypeptide having nitrilase activity, selected from the group of:
  a) a nucleic acid sequence having the sequence depicted in SEQ ID NO: 1,
  b) nucleic acid sequences which are derived from the nucleic acid sequence depicted in SEQ ID NO: 1 as a result of the degeneracy of the genetic code,
  c) derivatives of the nucleic acid sequence depicted in SEQ ID NO: 1, which code for polypeptides having the amino acid sequences depicted in SEQ ID NO: 2 and have at least 95% homology at the amino acid level, with negligible reduction in the enzymatic action of the polypeptides.

Homologs of the nucleic acid sequence according to the invention with sequence SEQ ID NO: 1 mean, for example, allelic variants which have at least 95% homology at the derived amino acid level, preferably at least 97% homology, very particularly preferably at least 98% homology, over the entire sequence range. It is possible and advantageous for the homologies to be higher over regions forming part of the sequences. The amino acid sequence derived from SEQ ID NO: 1 is to be seen in SEQ ID NO: 2. Allelic variants comprise, in particular, functional variants which are obtainable by deletion, insertion or substitution of nucleotides from the sequence depicted in SEQ ID NO: 1, and there ought to be a negligible reduction in the enzymatic activity of the derived synthesized proteins for the introduction of one or more genes into an organism however obtained [sic]. The invention thus also relates to amino acid sequences which are encoded by the group of nucleic acid sequences described above. The invention advantageously relates to amino acid sequences encoded by sequence SEQ ID NO: 1.

Homologs of SEQ ID NO: 1 also mean, for example, fungal or bacterial homologs, truncated sequences, single-stranded DNA or RNA of the coding and noncoding DNA sequence. Homologs of SEQ ID NO: 1 have at the DNA level a homology of at least 60%, preferably of at least 70%, particularly preferably of at least 80%, very particularly preferably of at least 90%, over the entire DNA region indicated in SEQ ID NO: 1.

Homologs of SEQ ID NO: 1 additionally mean derivatives such as, for example, promoter variants. The promoters which precede the stated nucleotide sequences can be modified by one or more nucleotide exchanges, by insertion(s) and/or deletion(s) without, however, adversely affecting the functionality or effectiveness of the promoters. The promoters may moreover have their effectiveness increased by modifying their sequence or be completely replaced by more effective promoters even from organisms of different species.

Derivatives also mean variants whose nucleotide sequence in the region from −1 to −200 in front of the start codon or 0 to 1000 base pairs after the stop codon have [sic] been modified in such a way that gene expression and/or protein expression is altered, preferably increased.

SEQ ID NO: 1 or its homologs can advantageously be isolated by methods known to the skilled worker from bacteria, preferably from Gram-negative bacteria, particularly preferably from bacteria of the genus Alcaligenes, very particularly preferably from bacteria of the genus and species *Alcaligenes faecalis*.

SEQ ID No: 1 or its homologs or parts of these sequences can be isolated from other fungi or bacteria for example using conventional hybridization processes or the PCR technique. These DNA sequences hybridize under standard conditions with the sequences according to the invention. The hybridization is preferably carried out with short oligonucleotides of the conserved regions, for example from the active center, and these can be identified in a manner known to the skilled worker by comparisons with other nitrilases or nitrile hydratases. However, it is also possible to use longer fragments of the nucleic acids according to the invention or the complete sequences for the hybridization. These standard conditions vary depending on the nucleic acid oligonucleotide [sic] used, longer fragment or complete sequence, or depending on which type of nucleic acid, DNA or RNA, are [sic] used for the hybridization. Thus, for example, the melting temperatures of DNA:DNA hybrids are about 10° C. lower than those of DNA:RNA hybrids of the same length.

Standard conditions mean, for example depending on the nucleic acid, temperatures between 42 and 58° C. in an aqueous buffer solution with a concentration between 0.1 to [sic] 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids advantageously comprise 0.1×SSC and temperatures 3 between about 20° C. to [sic] 45° C., preferably between about 30° C. to [sic] 45° C. The hybridization conditions for DNA:RNA hybrids preferably comprise 0.1×SSC and temperatures between about 30° C. to [sic] 55° C., preferably between about 45° C. to [sic] 55° C. These temperatures stated for the hybridization are melting temperatures calculated by way of example for a nucleic acid with a length of about 100 nucleotides and a G+C content of 50% in the absence of formamide. The experimental conditions for the DNA hybridization are described in relevant textbooks of genetics such as, for example, Sambrook et al., "Molecular Cloning", Cold Spring Harbor Laboratory, 1989, and can be calculated by formulae known to the skilled worker, for example depending on the length of the nucleic acids, the nature of the hybrids or the G+C content. The skilled worker can find further information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

The nucleic acid construct according to the invention means the nitrilase gene of sequence SEQ ID No. 1 and its homologs, which have advantageously been functionally linked to one or more regulatory signals to increase gene expression. These regulatory sequences are, for example, sequences to which the inducers or repressors bind and thus regulate the expression of the nucleic acid. In addition to these novel regulatory sequences, it is also possible for the natural regulation of these sequences to be present in front of the actual structural genes and, where appropriate, to have been genetically modified so that the natural regulation is switched off and the expression of the genes has been increased. The nucleic acid construct may, however, also have a simpler structure, that is to say no additional regulatory signals have been inserted in front of the sequence SEQ ID No. 1 or its homologs, and the natural promoter with its regulation has not been deleted. Instead, the natural regulatory sequence is mutated in such a way that the regulation no longer takes place, and gene expression is increased. The nucleic acid construct may additionally advantageously comprise one or more enhancer sequences, which make increased expression of the nucleic acid sequence possible, functionally linked to the promoter. It is also possible to insert advantageous additional sequences at the 3' end of the DNA sequences, such as other regulatory elements or terminators. The nucleic acids according to the invention may be present in one or more copies in the construct. The construct may also comprise further markers such as antibiotic resistances or auxotrophy-complementing genes where appropriate for selection of the construct.

Advantageous regulatory sequences for the process according to the invention are, for example, present in promoters such as cos, tac, trp, tet, trp-tet, lpp, lac, lpp-lac, lacI$^q$, T7, T5, T3, gal, trc, ara, SP6, λ-P$_R$ or the λ-P$_L$ promoter, which are advantageously used in Gram-negative bacteria. Further advantageous regulatory sequences are in, for example, the Gram-positive promoters amy and SPO2, in the fungal or yeast promoters ADC1, MFα, AC, P-60, CYC1, GAPDH, TEF, rp28, ADH. Also advantageous in this connection 45 are the promoters of pyruvate decarboxylase and of methanol oxidase from, for example, Hansenula. It is also possible to use artificial promoters for the regulation.

The nucleic acid construct is advantageously inserted into a vector such as, for example, a plasmid, a phage or other DNA for expression in a host organism, which makes optimum expression of the genes in the host possible. These vectors represent a further development of the invention. Examples of suitable plasmids in E. Coli are pLG338, pACYC184, pBR322, pUC18, pUC19, pKC30, pRep4, pHS1, pHS2, pPLc236, pMBL24, pLG200, pUR290, pIN-III$^{113}$-B1, λgt11 or pBdCI, in Streptomyces are pIJ101, pIJ364, pIJ702 or pIJ361, in Bacillus are pUB110, pC194 or pBD214, in Corynebacterium are pSA77 or pAJ667, in fungi are pALS1, pIL2 or pBB116, in yeasts are 2μM, pAG-1, YEp6, YEp13 or pEMBLYe23 or in plants are pLGV23, pGHlac$^+$, pBIN19, pAK2004 or pDH51. Said plasmids represent a small selection of the possible plasmids. Further plasmids are well known to the skilled worker and can be found, for example, in the book Cloning Vectors (eds. Pouwels P. H. et al. Elsevier, Amsterdam-N.Y.-Oxford, 1985, ISBN 0 444 904018).

The nucleic acid construct advantageously also contains, for expression of the other genes present, in addition 3' and/or 5' terminal regulatory sequences to increase expression, which are selected for optimal expression depending on the selected host organism and gene or genes.

These regulatory sequences are intended to make specific expression of the genes and of [sic] protein expression possible. This may mean, for example depending on the host organism, that the gene is expressed or overexpressed only after induction, or that it is immediately expressed and/or overexpressed.

The regulatory sequences or factors may moreover preferably influence positively, and thus increase, expression of the introduced genes. Thus, enhancement of the regulatory elements can take place advantageously at the level of transcription, by using strong transcription signals such as promoters and/or enhancers. However, it is also possible in addition to enhance translation by, for example, improving the stability of the mRNA.

In another embodiment of the vector, the vector comprising the nucleic acid construct according to the ivnention or the nucleic acid according to the invention can also advantageously be introduced in the form of a linear DNA into the microorganisms and be integrated by heterologous or homologous recombination into the genome of the host organism. This linear DNA may consist of a linearized vector such as a plasmid or only of the nucleic acid construct or of the nucleic acid.

For optimal expression of heterologous genes in organisms, it is advantageous to modify the nucleic acid sequences to accord with the codon usage specifically used in the organism. The codon usage can easily be established on the basis of computer analyses of other known genes in the relevant organism.

Suitable host organisms for the nucleic acid according to the invention or the nucleic acid construct are in principle all procaryotic or eucaryotic organisms. The host organisms advantageously used are microorganisms such as bacteria, fungi or yeasts. It is advantageous to use Gram-positive or Gram-negative bacteria, preferably bacteria of the family Enterobacteriaceae or Nocardiaceae, particularly preferably bacteria of the genera Escherichia, Pseudomonas or Rhodococcus. Very particular preference is given to the genus and species Escherichia coli.

The host organism according to the invention moreover preferably comprises at least one proteinaceous agent for folding the polypeptides it has synthesized and, in particular, the nucleic acid sequences having nitrilase activity described in this invention and/or the genes encoding this agent, the amount of this agent present being greater than that corresponding to the basic amount in the microorganism considered. The genes coding for this agent are present in the chromosome or in extrachromosomal elements such as, for example, plasmids.

EXAMPLES

Example 1

Purification of the Nitrilase from Alcaligenes Faecalis 1650

1. Production of the Cells

Alcaligenes faecalis 1650 was cultivated with shaking in culture medium A at 30° C. for a period of 8 hours.

| Culture medium A: | |
|---|---|
| Yeast extract | 5 g/l |
| Peptone | 3.5 g/l |
| $CH_3CO_2NH_4$ | 5 g/l |
| $KH_2PO_4$ | 5 g/l |
| $MgSO_4$ | 0.2 g/l |
| $FeSO_4$ | 0.03 g/l |
| NaCl | 1 g/l |
| Butyronitrile | 1 g/l |

200 ml of this preculture were used to inoculate a 10 l fermenter containing 8 l of fresh medium A. The pH, the temperature, the air flow rate and the stirring speed were 7.2, 30° C., 300 l/h and 300 rpm. After 22 h, 81 g of wet biomass were obtained. This corresponds to a dry weight of cells of 3.8 g/l and an optical density at 600 nm of 8.

2. Determination of the Enzymatic Activity for Mandelonitrile

The cells were obtained as described in Example 1 and washed twice in 10 mM Na/K phosphate buffer, pH 7.2. 40 mg dry weight of cells were resuspended in 20 ml of 10 mM Na/K phosphate buffer, pH 6.8, and the reaction was started by adding 8.3 mM mandelonitrile. The reaction was carried out at 400C with shaking. The kinetics of the racemate resolution were followed by taking samples and subsequently removing cells with the aid of high performance liquid chromatography (ODS Hypersil). Mandelonitrile, benzaldehyde, mandelamide and mandelic acid were determined in this case. The results are depicted in FIG. 1 [conversion of mandelonitrile into mandelic acid, batch]. The rate of formation of mandelic acid is 41.3 U/g dry weight of cells with 30% conversion, where 1 U is defined as the formation of 1 μmol of mandelic acid per minute at 40° C.

3. Determination of the Enzymatic Selectivity for Mandelonitrile

The cells were obtained as described in Example 1 and washed twice in 10 mM Na/K phosphate buffer, pH 7.2. 40 mg dry weight of cells were resuspended in 20 ml of 10 mM Na/K phosphate buffer, pH 6.8, and the reaction was started by adding 8.3 mM mandelonitrile. The reaction was carried out with shaking at 30° C. The kinetics were followed by taking samples and subsequently removing cells with the aid of high performance liquid chromatography (Nucleodex β-PM). S—(+)— and R—(−)-mandelic acid was determined in this case. The optical purity of the R—(−)-mandelic acid formed ($ee_{R-MA}$) was 98% at 50% conversion. The selectivity of the enzyme (=E) was 499 at 50% conversion.

4. Purification

Unless otherwise stated, 10 mM DTT was present in all the buffers during the purification.

Step 1: Cell Disruption

Cells were obtained as described in Example 1 from two 10 l fermentations in each case. The yield was about 162 g wet weight of cells. In each case 81 g wet weight of cells were resuspended in 160 ml of 0.1 M Tris/HCl buffer, pH 7.2, and disrupted four times in a Menton-Gaulin [sic] under 750 bar. The homogenate was then centrifuged at 30,000 g for 39 min, and the pellet was discarded. The supernatant (140 ml) had a remaining activity of 73%, as shown in Tab. 1.

Step 2: Ion Exchange Chromatography

The supernatant was diluted to 400 ml with buffer A (20 mM Tris/Cl, pH 8.5) and centrifuged once more at 23,000 g for 20 min. 350 ml were then loaded onto a Q-Sepharose column (diameter 5 cm, height 22 cm, volume 432 ml, Q-Sepharose Fast Flow from Pharmacia) in buffer A. Initially 10% buffer B (as buffer A with 1 M NaCl) was used for washing at a flow rate of 20 ml/min (total loading and washing volume corresponded to 1.5 l). The ratio was increased to 60% B linearly over the course of 90 min. 100% buffer B was then used for washing from 91 to 120 min. 100 40 ml fractions were collected. The nitrilase eluted between fractions 50 and 60. The fractions were combined and concentrated to a volume of 10 ml by ultrafiltration through a 10 kDa membrane (Amicon).

Step 3: Molecular Sieve Chromatography

The concentrate from the ion exchange chromatography (step 2) was further purified in two portions each of 5 ml by molecular sieve chromatography (Superdex 200 prep. grade, Pharmacia, separation range 10 to 600 kDa, diameter 2.6 cm, height 60 cm, volume 325 ml). Detection took place at 280 nm. The column was equilibrated in 20 mM phosphate buffer, pH 7.4, 5 mM DTT and 150 mM NaCl and was operated with a flow rate of 1.5 ml/min. 40 fractions were collected. The nitrile-hydrolyzing activity was found in fractions 3 to 5.

Step 4: Ion Exchange Chromatography

The combined fractions from the molecular sieve chromatography (step 3) were purified further by ion exchange chromatography on a Mono Q column (column volume 1 ml, Mono Q HR515, Pharmacia). The buffer A used was 20 mM Tris/HCl, pH 6.5, 5 mM DTT, and buffer B was the same buffer as in A with 1 M NaCl. The flow rate was 1 ml/min. The active fraction from the molecular sieve chromatography (about 100 ml) was diluted to a conductivity of about 6 mS/cm and was loaded directly onto the Mono Q column, and the protein was thus adsorbed. The column was washed with 5% buffer B after loading. The column was eluted with a gradient from 5% to 40% B in 30 min, followed by 100% B for 10 minutes. The nitrilase was eluted in fractions 17 and 18 of the gradient.

Steps 1–4 of the Purification are Represented in Table I.

TABLE I

Purification scheme

| Sample | Vol. [ml] | Activity [U/l] | Total activity [mU] | Yield [%] | Protein [mg/ml] | Total protein [mg] | Spec. activity [U/g] |
|---|---|---|---|---|---|---|---|
| before disruption | 160 | 480 | 76,800 | 100 | — | — | — |
| after disruption | 140 | 400 | 56,000 | 72.9 | — | — | — |
| Q-Sepharose | | | | | | | |
| Loaded | 140 | 192 | 26,880 | 35 | 12.4 | 1736 | 15 |
| AF | 400 | 77 | 30,800 | 40.1 | 0.26 | 104 | 296 |
| Superdex 200 | | | | | | | |
| Loaded | 9.5 | >378 | >3591 | 4.7 | 2.41 | 22.90 | >157 |
| AF | 43 | 59 | 2537 | 3.3 | 0.21 | 9.03 | 281 |

TABLE I-continued

Purification scheme

| Sample | Vol. [ml] | Activity [U/l] | Total activity [mU] | Yield [%] | Protein [mg/ml] | Total protein [mg] | Spec. activity [U/g] |
|---|---|---|---|---|---|---|---|
| MonoQ | | | | | | | |
| Loaded | 100 | 4.8 | 480 | 0.6 | 0.06 | 6.33 | 76 |
| AF | 4 | >77 | 308 | 0.4 | 0.19 | 0.76 | >405 |

Figure 2:
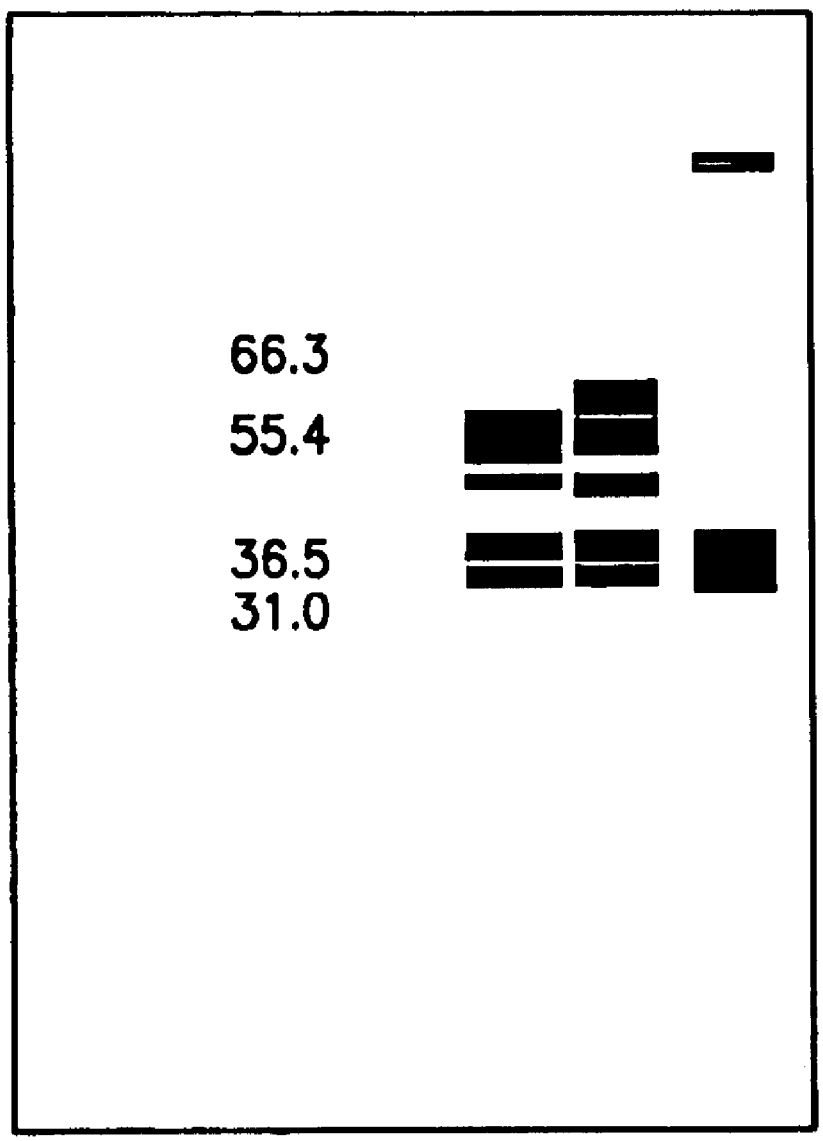
FIG. 2 depicts the fractionation by SDS-PAGE of active fractions from a molecular sieve chromatography and an ion exchange chromatography on Mono Q.

The active fractions it (=AF, Table I) from the molecular sieve chromatography (step 3) and ion exchange chromatography on Mono Q (step 4) have been fractionated by SDS-PAGE as depicted in FIG. 2.

Step 5: Reversed Phase (RP) High [Lacuna] Liquid Chomatography

The active fraction (fractions 17 and 18) of the Mono Q chromatrography (step 4) were checked for homogeneity by RP chromatography and further purified to prepare for trypsin cleavage. The separation was carried out with an Abimed column (3 cm) on a Hewlett-Packard apparatus (HP 1090). The mobile phase used was buffer A: water with 0.1% TFA and buffer B: acetonitrile with 0.1% TFA. Volume injected 0.1 ml, flow rate 0.5 ml/min. The elution gradient had the following profile:

| Minute | % buffer A | % buffer B |
|---|---|---|
| 0 | 80 | 20 |
| 2 | 80 | 20 |
| 22 | 30 | 70 |
| 22.1 | 0 | 100 |
| 24 | 0 | 100 |
| 25 | 100 | 0 |
| 30 | 100 | 0 |

The nitrilase eluted between 12 and 13 minutes. This corresponds to a 37 kDa band in the SDS-PAGE. This band was partially sequenced using the Applied Biosystems 494 Procise protein sequencer. The N-terminal sequence of 39 amino acids obtained in this way is referred to as SEQ ID NO: 3 hereinafter. The sequence is included in the appended list of sequences and is: Met Gln Thr Arg Lys Ile Val Arg Ala Ala Ala Val Gln Ala Ala Ser Pro Asn Tyr Asp Leu Ala Thr Gly Val Asp Lys Thr Ile Glu Leu Ala Arg Gln Ala Arg Asp Glu Gly.

Preparation of Tryptic Peptides

The sample from the Mono Q chromatography (step 4) was pretreated as follows: the protein (about 0.6 mg) was precipitated with 12.5% TCA and the pellet was washed three times with 1 ml of ether/ethanol (1:1). The pellet was dissolved in 0.2 ml of 6 M guanidine HCl, 25 mm tris/HCl, pH 8.5. 2.6 µl of a 1 M DTT solution were added to this solution to reduce the disulfite [sic] bridges. The sample was shaken in the dark for 1 hour. The protein was then reacted with 1.5 µl of a 4-vinylpyridine solution (35%) in the dark for 2 hours. The reaction was stopped by incubating with 2.6 µl of a 1 M DTT solution for 1 hour. The vinylpyrrilidated [sic] enzyme was purified by RP-HPLC as described above. The retention time was now between 10 and 11 minutes. The active fraction, identified by its molecular weight, was collected and concentrated to 0.02 ml. This was adjusted to 0.2 ml by adding 0.01 ml of acetonitrile and 0.1 M Tris/HCl, pH 8.5. The pH was corrected by also adding about 0.05 ml of 0.1 M NaOH. The sample (estimated amount of protein 0.3 mg) was mixed with 0.032 ml of a 1 mg/ml trypsin solution in 0.1 M Tris/HCl, pH 8.5, 5% acetonitrile, and incubated at 37° C. overnight. The digestion was stopped with 0.01 ml of acetic acid, followed-by centrifugation. The supernatant was separated by RP-HPLC on C18 (eluent system: buffer A: water, 0.1% TFA, buffer B: acetonitrile, 0.1% TFA). Peptides (detection at 205 nm and 280 nm) were collected and sequenced. The Applied Biosystems 494 Procise protein sequencer was used. The internal peptide sequence of 21 amino acids is referred to hereinafter as SEQ ID NO: 4 and the internal peptide sequence of 11 amino acids is referred to as SEQ ID NO: 5. SEQ ID NO: 4 and 5 are included in the appended list of sequences and are:

SEQ ID NO: 4

Glu Glu Ala Pro Glu Gln Gly Val Gln Ser Lys Ile Ala Ser Val Ala Ile Ser His Pro Gln

SEQ ID NO: 5

Glu Glu Ala Pro Glu Gln Gly Val Gln Ser Lys

6. Activity of the Purified Nitrilase for Mandelonitrile

The activity of the purified nitrilase for mandelonitrile was investigated as described in Example 2. The specific activity of the purified protein for mandelonitrile was 12,380 U/g of protein.

Example 2

Cloning of the Nitrilase from *Alcaligenes Faecalis* 1650

Nucleotide probes were derived from the peptide sequences SEQ ID NO: 3 and 4 described in Example 1 and were synthesized. The nucleotide probe derived from SEQ ID NO: 3, the N-terminal peptide sequence, was a 64-fold degenerate 23 mer (in the sequence of the nucleotide probe, A, C, G or T is replaced by N; A or G by R; C or G by S). The high percentage of GC in the Alcaligenes strains described in the literature (Wada et al., 1992, Nucl. Acids Res., 20, 2111–2118) meant that in the case of glutamine and isoleucine the selection of the third position of the codon was predetermined. The nucleotide probe, which is referred to hereinafter as SEQ ID NO: 6, is the 5' primer for the subsequent PCR, where S=C or G and N=A, C, G or T, and is:

SEQ ID NO: 6

5'-ATGCAGACNAGNAARATCGTSCG-3'

A 256-fold degenerate 20 mer was derived as nucleotide probe from SEQ ID NO: 4, the internal peptide sequence (in the sequence of the nucleotide bases, A, C, G or T is replaced by N; A or G by R; C or G by S). The high percentage of GC in the Alcaligenes strains meant that in the case of lysine the selection of the third position of the codon was predetermined. This nucleotide probe is the 3' primer for the subsequent PCR and is referred to hereinafter as SEQ ID NO: 7. It is included in the appended list of sequences and is:

SEQ ID NO: 7

5'-TNGCSACNGANGCRATCTTG-3'

This pair of primers, SEQ ID NO: 6 and 7, was used to carry out the PCR on chromosomal DNA from *Alcaligenes faecalis* 1650. Isolation of chromosomal DNA took place after cell lysis with lysozyme and proteinase K treatment by the classical method known to the skilled worker (Ausubel, F. M. et al. (1994) Current protocols in molecular biology, John Wiley and Sons). The PCR using Pwo polymerase comprised denaturation at 95° C. for 3 min; 35 cycles with denaturation at 95° C. for 1 min, primer annealing at 58° C.

for 1 min 30 sec and polymerization at 72° C. for 1 min 30 sec; and a concluding polymerization at 72° C. for 5 min. Under these conditions, a fragment about 1 kb in size was amplified from the chromosomal DNA from *Alcaligenes faecalis* 1650. To clone the PCR product, an XbaI restriction cleavage site and two additional nucleotides (5'-AATCTAGA and 5'-ATTCTAGA) were attached to each of the primers mentioned above, and the PCR reaction was repeated under the abovementioned conditions. Once again there was amplification of a fragment about 1 kb in size which, after purification and XbaI digestion, was ligated into analogously digested puC18. After transformation of *E. coli* JM109 and isolation of the resulting plasmid, the DNA was purified by sequencing and subsequent genomic Southern blot. The molecular biological and microbiological methods for isolating the complete nitrilase gene (nit) took place by the classical methods [sic] known to the skilled worker. The complete nitrilase sequence is depicted in SEQ ID NO: 1.

Example 3

Homology with Other Proteins, Identification of the Homologous Sequence

Comparison with the sequences from the SWISSPROT protein database showed that the nitrilase gene in this invention has 11 to 96% homology with known nitrilases at the amino acid level. The greatest sequence homology was found with the arylacetonitrile-specific nitrilase from Alcalignes [sic] *faecalis* JM3 (Nagasawa et al., Eur. J. Biochem. 1990, 194, 765–772). The two nitrilase genes have an identity of 93.2% at the nucleotide level over a region of 1071 bp. The derived amino acid sequence has an identity of 96.1% over a region of 356 amino acids. The smallest homology of 11.4% over a region of 534 amino acids was found with the nitrilase from *Rhodococcus erythropolis* SK92 (EP-A-0 719 862).

Example 4

Heterologous Expression of the Nitrilase in *E. coli*

The nit gene was amplified for cloning into the expression vector pJOE2702. The 5' primer selected in this case for the PCR was the abovementioned SEQ ID NO: 3, with an NdeI cleavage site with overlaps with the translation start being attached at the nit 51 end. This primer is referred to hereinafter as SEQ ID NO: 8 and is included in the appended list of sequences. The 3' primer selected was a 24 mer from the 3' region of the nit gene, with a BamHI cleavage sites [sic] adjacent to the stop codon being attached. It is referred to hereinafter as SEQ ID NO: 9 and is included in the subsequent list of sequences.

5'-TTAATCATATGCAGACAAGAAAAATCGTCCG-3' (=SEQ ID NO: 8) 5'-AAGGATCCTCAAGACG-GCTCTTGCACTAGCAG-3' (=SEQ ID NO: 9)

Figure 3:
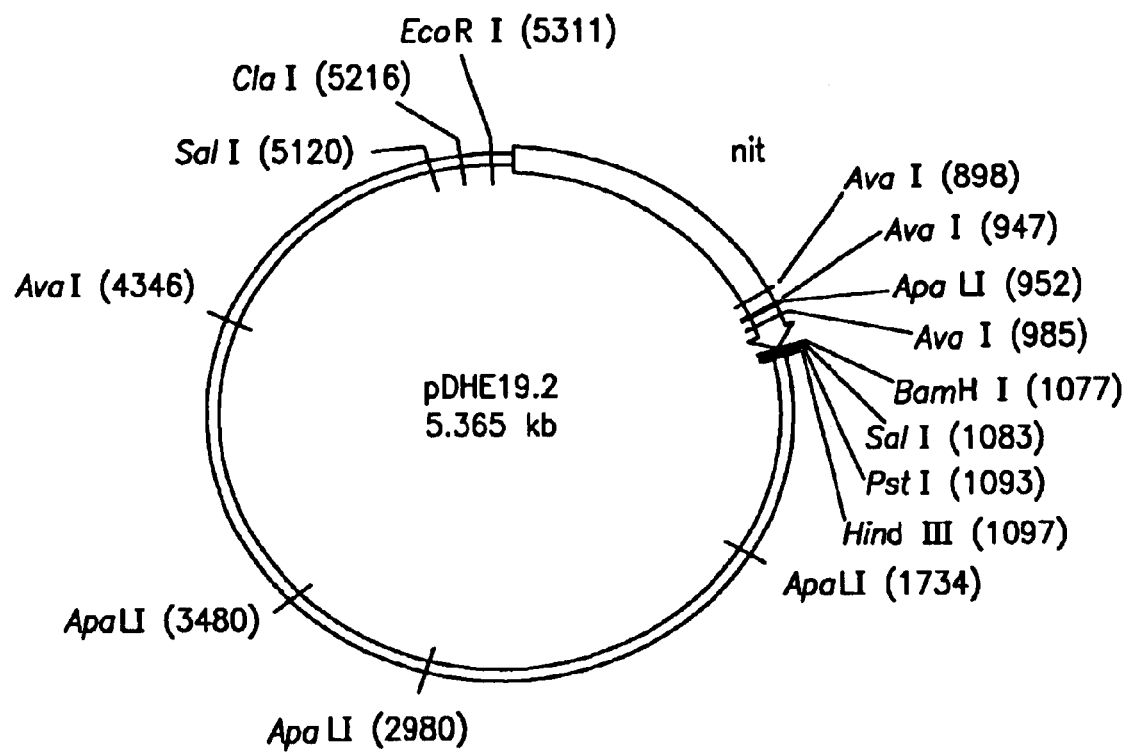
FIG. 3 depicts the plasmid, called pDHE19.2, resulting from purification of a PCR fragment, digestion with NdeI/BamHI and integration into the analogously digested vector pJOE2702.

The PCR using Pwo polymerase comprised a denaturation at 94° C. for 3 min; 25 cycles with a denaturation at 93° C. for 1 min, a primer annealing at 55° C. for 1 min 30 sec and a polymerization at 72° C. for 1 min 30 sec, and a final polymerization at 72° C. for 5 min. The resulting PCR fragment was purified, digested with NdeI/BamHI and integrated into the analogously digested vector pJOE2702 (Volff et al., 1996, Mol. microbiol., 21(5), 1037–1047). The resulting plasmid was called pDHE 19.2 and is depicted in FIG. 3. The integration via the NdeI/BamHI cleavage sites means that in the plasmid pDHE19.2 the nit gene is under transcription control of the promoter rhap which is present in pJOE2702 and originates from the positively regulated L-rhamnose operon rhaBAD in *E. coli* (Egan & Schleif, 1994, J.Mol. Biol., 243, 821–829). Termination of transcription of the nit gene and initiation of translation likewise take place via vector sequences. In addition, the plasmid contains a gene which confers ampicillin resistance $Ap^R$.

Heterologous expression of the nitrilase was shown with the *E. coli* JM109 strain containing the plasmid pDHE19.2. For this 40 purpose, the strain JM109 (pDHE19.2) was cultured in the TB culture medium with 100 µg/ml ampicillin (Tartof, Hobbs 1987 [sic] with shaking at 37° C. At an $OD_{600}$ of 1.7, the culture was transferred 1:200 into fresh TB medium which contained 0.2% (w/v) L-rhamnose to induce the nitrilase, and was cultivated with shaking at 30° C. After 8 hours, the cells were harvested, washed with 10 mM Na/K phosphate buffer, pH 7.2, resuspended in the same buffer to an $OD_{600}$ of 10, and disrupted after [sic] treatment with ultrasound.

Example 5

Determination of the Nitrilase Activity of the recombinate [sic] strain *E. coli* JM109 (pDHE19.2)

1. Production of the Cells

*E. coli* JM109 (pDHE19.2) was cultivated in TB medium+100 µg/ml ampicillin with shaking at 37° C. for 6 hours. At an $OD_{600}$ of 4, 100 ml of this preculture were used to inoculate a 10 l fermenter containing 8l of fresh TB medium+100 µg/ml ampicillin+2 g/l L-rhamnose. The pH, the temperature, the air flow rate and the stirring speed were 7.2, 30° C., 300 l/h and 400–650 rpm. The cells were harvested after 16 hours. The optical density at 600 nm at this time was 18, corresponding to a dry weight of cells of 7.8 g/l.

2. Determination of the Specific Activity for Mandelonitrile

The cells were obtained as described in Example 1 and washed in 10 mM Na/K phosphate buffer, pH 7.2. 2 mg dry weight of cells were resuspended in 1 ml 10 mM Na/K phosphate buffer, pH 7.2, and the reaction was started by adding 8.3 mM mandelonitrile. The reaction was carried out with shaking at 40° C. The kinetics were followed by taking samples and subsequent high performance liquid chromatography (ODS Hypersil). Mandelonitrile, benzaldehyde, mandelamide and mandelic acid were determined. The rate of formation of mandelic acid is 403 U/g dry weight of cells with a conversion of 30%, 1 U being defined as the formation of 1 µmol of mandelic acid per minute at 40° C.

Example 6

Figure 4:
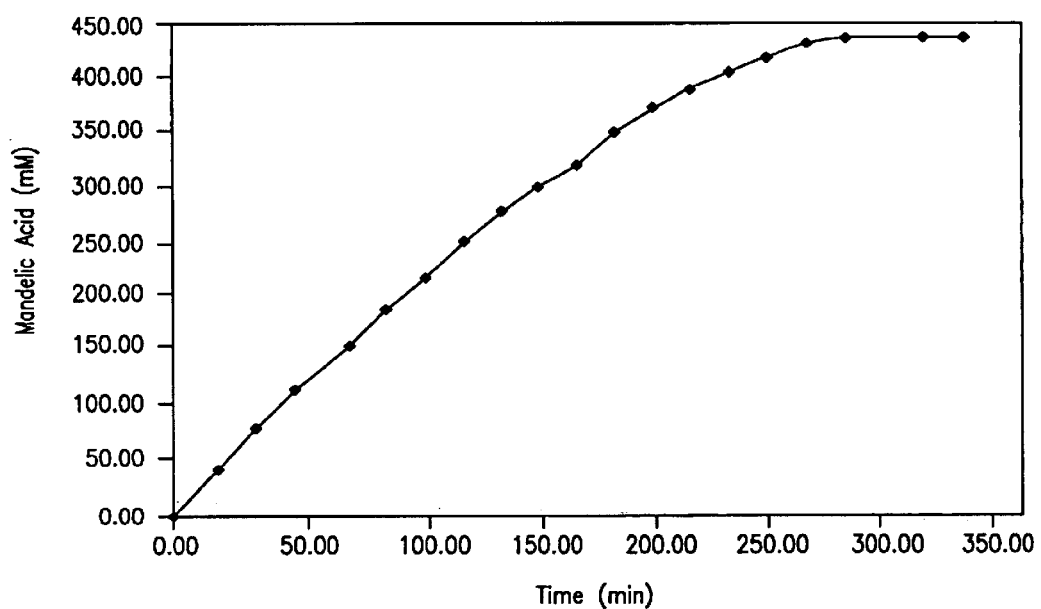
FIG. 4 depicts the synthesis of R-mandelic acid by hydrolysis of mandelonitrile using E. coli JM109 (pDHE19.2) in suspension, as a function of time.

Synthesis of R-mandelic Acid by Hydrolysis of Mandelonitrile using *E. coli* JM109 (pDHE19.2) in Suspension Mandelonitrile in a concentration of 1.3 g/l was metered over the course of 10 hours into a volume of 1 l of 10 mM Na/K phosphate buffer, pH 7.2, which contained the strain *E. coli* JM109 (pDHE19.2) in a concentration of 2 g/l while stirring with a paddle stirrer at 40° C. The metering was controlled via the nitrile consumption. The rate of consumption of R-mandelic acid was followed as described in Example 5. The results are depicted in FIG. 4.

Example 7

Isolation of R-mandelic Acid by Extraction from the Reaction Mixture from the Hydrolysis of Mandelonitrile by *E. coli* [sic] JM109 (pDHE19.2) in Suspension The aqueous mandelic acid reaction mixture obtained in Example 6 was centrifuged to remove the cells, adjusted to pH 2 with an acid and extracted three times with methyl tert-butyl ether (MTBE). After removal of the organic solvent from the mandelic acid extract by evaporation, the resulting white mandelic acid crystals were redissolved and investigated for chemical and optical purity by high performance liquid chromatography. The chemical purity was 99%, and the optical purity of the R-mandelic acid was 97.4%ee.

Example 8

Isolation of R-mandelic Acid by Crystallization with Cooling from the Reaction Mixture from the Hydrolysis of Mandelonitrile by *E. coli* JM109 (pDHE19.2) in Suspension The aqueous mandelic acid reaction mixture obtained in Example 6 was centrifuged to remove the cells, concentrated to 40% of the initial volume with heating and stirring and adjusted to pH 2 with an acid. The mandelic acid was crystallized out by cooling in an ice bath, and the resulting white mandelic acid crystals were filtered off with suction and dried. The crystals were redissolved and investigated for chemical and optical purity by high performance liquid chromatography. The chemical purity was 99.1%, and the optical purity of the R-mandelic acid was 99.8%ee.

Example 9

Conversion of Various Nitriles

The *E. coli* strain (see Example 6) or the initial Alcaligenes strain was used to convert various nitriles. The Alcaligenes cells were cultured in 400 ml Alcaligenes medium (see medium A above) at 30° C. and 160 rpm for 16 hours (=h) [sic]. The cells were harvested by centrifugation (4° C. and 5000 rpm, 30 min). 150 μl portions of a cell suspension were pipetted into each of the wells of the microtiter plate. The plate was then centrifuged. The supernatant was aspirated off and the cell pellets were washed twice with $Na_2HPO_4$ (1.42 g/l in Finnaqua, pH 7.2). The substrate solution (150 μl) was then pipetted, and the cells were resuspended. One substrate was added to each row of 12 holes in the microtiter plate. A row with the substrate solution but without cells was used as control (=blank).

Figure 5:
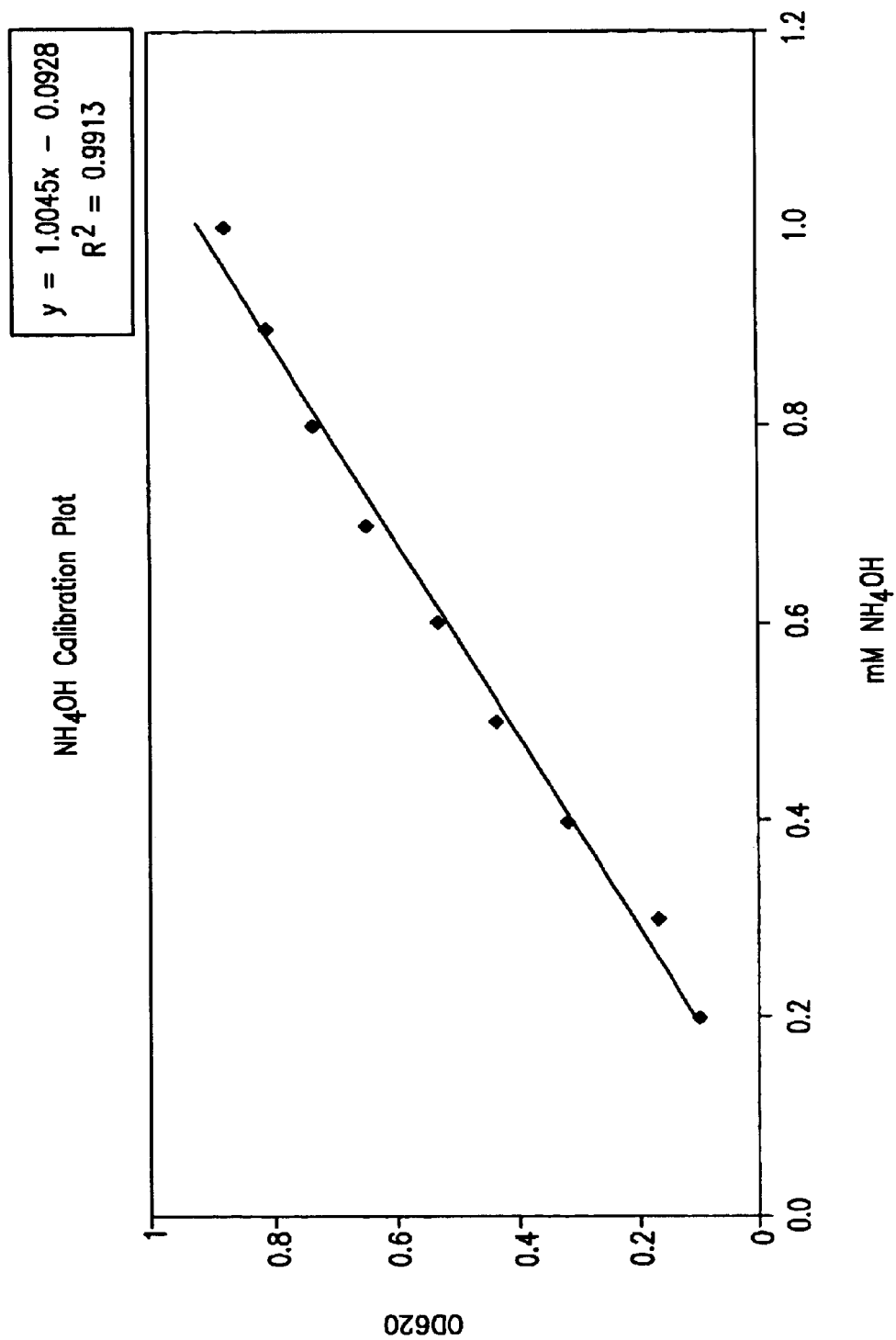
FIG. 5 depicts a calibration plot constructed with various $NH^4OH$ solutions.

The microtiter plates were left in a shaking incubator at 200 rpm and 30° C. for 2 hours. The cells were then centrifuged down, and the amount of $NH_4$ ions produced in the supernatant was determined using a Biomek apparatus. The measurement took place at 620 nm using a calibration plot constructed with various $NH_4OH$ solutions (see FIG. 5). The substrates used were mandelonitrile (=1), 2-phenylpropionitrile (=2), 2-phenylbutyronitrile (=3), benzyl cyanide (=4), 4-chlorobenzyl cyanide (=5), 4-bromobenzyl cyanide (=6), propionitrile (=7), 2-methylbutyronitrile (=8, 2-cyanobutane), geranonitrile (=9), valeronitrile (=10), 3-cyanopyridine (=11), 3-biphenyl-2-hydroxybutyronitrile [sic] (=12), 4-flourobenzyl [sic] cyanide (=13, 4-fluorophenylacetro-nitride [sic]) and α-(3-heptyl)-nitro-triacetonitrile (=14). A 0.2 molar stock solution in methanol was made up for each of the subtrates, and this was diluted to 10 mM with $Na_2HPO_4$ (1.42 g/l in Finnagua, pH 7.2). The cell suspensions were standardized to 2 g/l dry biomaass. Table II shows the averages for a microtiter plate row in the conversion.

TABLE II

Conversion of various nitriles with nitrilase 1650

| Substrate No. | μmol/l | Activity | % conversion |
|---|---|---|---|
| 1 | 2141.2 | 8.9 | 86.3 |
| 2 | 1001.1 | 4.1 | 70.2 |
| 3 | 24.4 | 0.1 | 44.3 |
| 4 | 2210.5 | 9.2 | 100 |
| 5 | 2136.3 | 8.9 | 100 |
| 6 | 1500.8 | 6.2 | 100 |
| 7 | 4.9 | 0.02 | NA |
| 8 | — | — | NA |
| 9 | — | — | NA |
| 10 | 113.4 | 0.47 | NA |
| 11 | — | — | NA |
| 12 | — | — | NA |
| 13 | 2222.9 | 9.2 | 100 |
| 14 | 84.8 | 0.35 | 44.1 |

Figure 6:
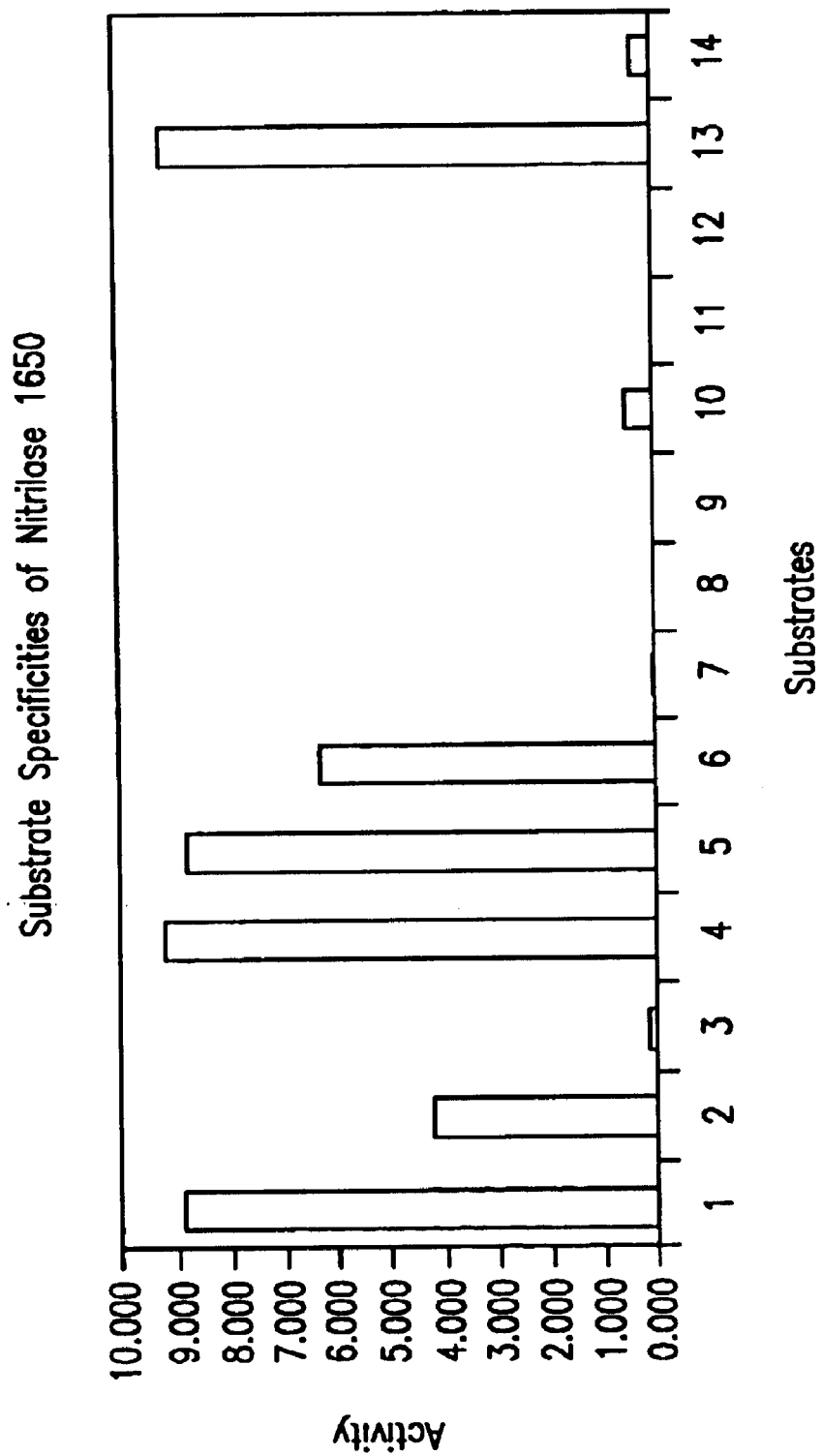
FIG. 6 depicts the activities of various substrates with nitrilase 1650.

FIG. 6 shows the results of the conversion as activities.

We claim:

1. An isolated nucleic acid which codes for a polypeptide having nitrilase activity, selected from the group consisting of:
   a) a nucleic acid depicted in SEQ ID NO: 1,
   b) a nucleic acid which codes for the polypeptide depicted in SEQ ID NO: 2,
   c) a nucleic acid, which codes for a polypeptides having at least 97% homology to SEQ ID NO 2, with negligible reduction in the enzymatic action of the polypeptides.

2. An isolated polypeptide encoded by a nucleic acid as claimed in claim 1.

3. An isolated polypeptide as claimed in claim 2, encoded by the nucleotide sequence depicted in SEQ ID NO: 1.

4. A nucleic acid construct comprising a nucleic acid as claimed in claim 1, the nucleic acid being linked to one or more regulatory sequences.

5. A vector comprising a nucleic acid as claimed in claim 1.

6. A transformed microorganism comprising at least one nucleic acid as claimed in claim 1.

7. A transformed microorganism comprising at least one nucleic acid as claimed in claim 1.

8. A process for preparing chiral carboxylic acids of the general formula I

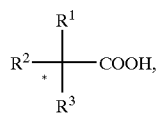
(I)

which comprises converting the corresponding racemic nitriles of the general formula II

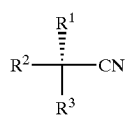
(II)

in the presence of an Isolated polypeptide or protein having the amino acid sequence of SEQ ID NO: 2, and where at least 25 mmol of nitrile are converted per h and per mg of protein, or 25 mmol of nitrile are converted per h and per g of dry weight, into the chiral carboxylic acids, where the substituents and variables in the formulae I and II have the following meanings:

an optically active center $R^1$, $R^2$, $R^3$ independently of one another hydrogen, substituted or unsubstituted, branched or unbranched $C_1$–$C_{10}$-alkyl, $C_2$–$C_{10}$-alkenyl, substituted or unsubstituted aryl, hetaryl, $OR^4$ or $NR^4R^5$ and where the radicals $R^1$, $R^2$ and $R^3$ are always different.

$R^4$ hydrogen, substituted or unsubstituted, branched or unbranched $C_1$–$C_{10}$-alkyl, $C_2$–$C_{10}$-alkenyl, $C_1$–$C_{10}$-alkylcarbonyl, $C_2$–$C_{10}$-alkenylcarbonyl, aryl, arylcarbonyl, hetaryl or hetarylcarbonyl, $R^5$ hydrogen, substituted or unsubstituted, branched or unbranched $C_1$–$C_{10}$-alkyl, $C_2$–$C_{10}$-alkenyl, aryl or hetaryl.

9. A process as claimed in claim 8, wherein one of the substituents $R^1$, $R^2$ or $R^3$ is $OR^4$.

10. A process as claimed in claim 8, wherein one of the substituents $R^1$, $R^2$ or $R^3$ is aryl.

11. A process as claimed in claim 8, wherein the process is carried out in an aqueous reaction solution at a pH between 4 and 11.

12. A process as claimed in claim 8, wherein from 0.01 to 10% by weight of nitrile or from 0.01 to 10% by weight of a corresponding aldehyde or ketone and from 0.01 to 10% by weight of hydrocyanic acid are reacted in the process.

13. A process as claimed in claim 8, wherein the process is carried out at a temperature between 0° C. and 80° C.

14. A process as claimed in claim 8, wherein the chiral carboxylic acid is isolated from the reaction solution in yields of from 60 to 100% by extraction or crystallization or extraction and crystallization.

15. A process as claimed in claim 8, wherein the chiral carboxylic acid has an optical purity of at least 90%.

* * * * *

SEQUENCE LISTING

<160> NUMBER OF SEQ ID NOS: 9

<210> SEQ ID NO 1
<211> LENGTH: 1071
<212> TYPE: DNA
<213> ORGANISM: Alcaligenes faecalis
<220> FEATURE:
<221> NAME/KEY: CDS
<222> LOCATION: 1 ... 1071

<400> SEQUENCE: 1

```
atg cag aca aga aaa atc gtc cgg gca gcc gcc gta cag gcc gcc tct      48
Met Gln Thr Arg Lys Ile Val Arg Ala Ala Ala Val Gln Ala Ala Ser
 1               5                  10                  15 ccc aac tac gat ctg gca acg ggt gtt gat aaa acc att gag ctg gct      96
Pro Asn Tyr Asp Leu Ala Thr Gly Val Asp Lys Thr Ile Glu Leu Ala
             20                  25                  30 cgt cag gcc cgc gat gag ggc tgt gac ctg atc gtg ttt ggt gaa acc     144
Arg Gln Ala Arg Asp Glu Gly Cys Asp Leu Ile Val Phe Gly Glu Thr
         35                  40                  45
```

```
tgg ctg ccc gga tat ccc ttc cac gtc tgg ctg ggc gca ccg gcc tgg    192
Trp Leu Pro Gly Tyr Pro Phe His Val Trp Leu Gly Ala Pro Ala Trp
 50                  55                  60 tcg ctg aaa tac agt gcc cgc tac tat gcc aac tcg ctc tcg ctg gac    240
Ser Leu Lys Tyr Ser Ala Arg Tyr Tyr Ala Asn Ser Leu Ser Leu Asp
 65                  70                  75                  80 agt gca gag ttt caa cgc att gcc cag gcc gca cgg acc ttg ggt att    288
Ser Ala Glu Phe Gln Arg Ile Ala Gln Ala Ala Arg Thr Leu Gly Ile
                 85                  90                  95 ttc atc gca ctg ggt tat agc gag cgc agc ggc ggc agc ctt tac ctg    336
Phe Ile Ala Leu Gly Tyr Ser Glu Arg Ser Gly Gly Ser Leu Tyr Leu
            100                 105                 110 ggc caa tgc ctg atc gac gac aag ggc gag atg ctg tgg tcg cgt cgc    384
Gly Gln Cys Leu Ile Asp Asp Lys Gly Glu Met Leu Trp Ser Arg Arg
        115                 120                 125 aaa ctc aaa ccc acg cat gta gag cgc acc gta ttt ggt gaa ggt tat    432
Lys Leu Lys Pro Thr His Val Glu Arg Thr Val Phe Gly Glu Gly Tyr
130                 135                 140 gcc cgt gat ctg att gtg tcc gac aca gaa ctg gga cgc gtc ggt gct    480
Ala Arg Asp Leu Ile Val Ser Asp Thr Glu Leu Gly Arg Val Gly Ala
145                 150                 155                 160 cta tgc tgc tgg gag cat ttg tcg ccc ttg agc aag tac gcg ctg tac    528
Leu Cys Cys Trp Glu His Leu Ser Pro Leu Ser Lys Tyr Ala Leu Tyr
                165                 170                 175 tcc cag cat gaa gcc att cac att gct gcc tgg ccg tcg ttt tcg cta    576
Ser Gln His Glu Ala Ile His Ile Ala Ala Trp Pro Ser Phe Ser Leu
            180                 185                 190 tac agc gaa cag gcc cac gcc ctc agt gcc aag gtg aac atg gct gcc    624
Tyr Ser Glu Gln Ala His Ala Leu Ser Ala Lys Val Asn Met Ala Ala
        195                 200                 205 tcg caa atc tat tcg gtt gaa ggc cag tgc ttt acc atc gcc gcc agc    672
Ser Gln Ile Tyr Ser Val Glu Gly Gln Cys Phe Thr Ile Ala Ala Ser
210                 215                 220 agt gtg gtc acc caa gag acg cta gac atg ctg gaa gtg ggt gaa cac    720
Ser Val Val Thr Gln Glu Thr Leu Asp Met Leu Glu Val Gly Glu His
225                 230                 235                 240 aac gcc ccc ttg ctg aaa gtg ggc ggc ggc agt tcc atg att ttt gcg    768
Asn Ala Pro Leu Leu Lys Val Gly Gly Gly Ser Ser Met Ile Phe Ala
                245                 250                 255 ccg gac gga cgc aca ctg gct ccc tac ctg cct cac gat gcc gag ggc    816
Pro Asp Gly Arg Thr Leu Ala Pro Tyr Leu Pro His Asp Ala Glu Gly
            260                 265                 270 ttg atc att gcc gat ctg aat atg gag gag att gcc ttc gcc aaa gcg    864
Leu Ile Ile Ala Asp Leu Asn Met Glu Glu Ile Ala Phe Ala Lys Ala
        275                 280                 285 atc aat gac ccc gta ggc cac tat tcc aaa ccc gag gcc acc cgt ctg    912
Ile Asn Asp Pro Val Gly His Tyr Ser Lys Pro Glu Ala Thr Arg Leu
290                 295                 300 gtg ctg gac ttg ggg cac cga gac ccc atg act cgg gtg cac tcc aaa    960
Val Leu Asp Leu Gly His Arg Asp Pro Met Thr Arg Val His Ser Lys
305                 310                 315                 320 agc gtg acc agg gaa gag gct ccc gag caa ggt gtg caa agc aag att    1008
Ser Val Thr Arg Glu Glu Ala Pro Glu Gln Gly Val Gln Ser Lys Ile
                325                 330                 335 gcc tca gtc gct atc agc cat cca cag gac tcg gac aca ctg cta gtg    1056
Ala Ser Val Ala Ile Ser His Pro Gln Asp Ser Asp Thr Leu Leu Val
            340                 345                 350 caa gag ccg tct tga                                                1071
Gln Glu Pro Ser
```

-continued

355

<210> SEQ ID NO 2
<211> LENGTH: 356
<212> TYPE: PRT
<213> ORGANISM: Alcaligenes faecalis

<400> SEQUENCE: 2

```
Met Gln Thr Arg Lys Ile Val Arg Ala Ala Val Gln Ala Ala Ser
 1               5                  10                  15

Pro Asn Tyr Asp Leu Ala Thr Gly Val Asp Lys Thr Ile Glu Leu Ala
            20                  25                  30

Arg Gln Ala Arg Asp Glu Gly Cys Asp Leu Ile Val Phe Gly Glu Thr
        35                  40                  45

Trp Leu Pro Gly Tyr Pro Phe His Val Trp Leu Gly Ala Pro Ala Trp
    50                  55                  60

Ser Leu Lys Tyr Ser Ala Arg Tyr Tyr Ala Asn Ser Leu Ser Leu Asp
65                  70                  75                  80

Ser Ala Glu Phe Gln Arg Ile Ala Gln Ala Ala Arg Thr Leu Gly Ile
                85                  90                  95

Phe Ile Ala Leu Gly Tyr Ser Glu Arg Ser Gly Gly Ser Leu Tyr Leu
            100                 105                 110

Gly Gln Cys Leu Ile Asp Asp Lys Gly Glu Met Leu Trp Ser Arg Arg
        115                 120                 125

Lys Leu Lys Pro Thr His Val Glu Arg Thr Val Phe Gly Glu Gly Tyr
    130                 135                 140

Ala Arg Asp Leu Ile Val Ser Asp Thr Glu Leu Gly Arg Val Gly Ala
145                 150                 155                 160

Leu Cys Cys Trp Glu His Leu Ser Pro Leu Ser Lys Tyr Ala Leu Tyr
                165                 170                 175

Ser Gln His Glu Ala Ile His Ile Ala Ala Trp Pro Ser Phe Ser Leu
            180                 185                 190

Tyr Ser Glu Gln Ala His Ala Leu Ser Ala Lys Val Asn Met Ala Ala
        195                 200                 205

Ser Gln Ile Tyr Ser Val Glu Gly Gln Cys Phe Thr Ile Ala Ala Ser
    210                 215                 220

Ser Val Val Thr Gln Glu Thr Leu Asp Met Leu Glu Val Gly Glu His
225                 230                 235                 240

Asn Ala Pro Leu Leu Lys Val Gly Gly Gly Ser Ser Met Ile Phe Ala
                245                 250                 255

Pro Asp Gly Arg Thr Leu Ala Pro Tyr Leu Pro His Asp Ala Glu Gly
            260                 265                 270

Leu Ile Ile Ala Asp Leu Asn Met Glu Glu Ile Ala Phe Ala Lys Ala
        275                 280                 285

Ile Asn Asp Pro Val Gly His Tyr Ser Lys Pro Glu Ala Thr Arg Leu
    290                 295                 300

Val Leu Asp Leu Gly His Arg Asp Pro Met Thr Arg Val His Ser Lys
305                 310                 315                 320

Ser Val Thr Arg Glu Glu Ala Pro Glu Gln Gly Val Gln Ser Lys Ile
                325                 330                 335

Ala Ser Val Ala Ile Ser His Pro Gln Asp Ser Asp Thr Leu Leu Val
            340                 345                 350

Gln Glu Pro Ser
        355
```

```
<210> SEQ ID NO 3
<211> LENGTH: 39
<212> TYPE: PRT
<213> ORGANISM: Alcaligenes faecalis

<400> SEQUENCE: 3

Met Gln Thr Arg Lys Ile Val Arg Ala Ala Val Gln Ala Ala Ser
 1               5                  10                  15

Pro Asn Tyr Asp Leu Ala Thr Gly Val Asp Lys Thr Ile Glu Leu Ala
            20                  25                  30

Arg Gln Ala Arg Asp Glu Gly
        35

<210> SEQ ID NO 4
<211> LENGTH: 21
<212> TYPE: PRT
<213> ORGANISM: Alcaligenes faecalis

<400> SEQUENCE: 4

Glu Glu Ala Pro Glu Gln Gly Val Gln Ser Lys Ile Ala Ser Val Ala
 1               5                  10                  15

Ile Ser His Pro Gln
            20

<210> SEQ ID NO 5
<211> LENGTH: 11
<212> TYPE: PRT
<213> ORGANISM: Alcaligenes faecalis

<400> SEQUENCE: 5

Glu Glu Ala Pro Glu Gln Gly Val Gln Ser Lys
 1               5                  10

<210> SEQ ID NO 6
<211> LENGTH: 23
<212> TYPE: DNA
<213> ORGANISM: Alcaligenes faecalis
<220> FEATURE:
<221> NAME/KEY: Unsure
<222> LOCATION: 1 ... 23
<223> OTHER INFORMATION: n represents g, a, t or c

<400> SEQUENCE: 6
atgcagacna gnaaatcgt scg                                        23

<210> SEQ ID NO 7
<211> LENGTH: 20
<212> TYPE: DNA
<213> ORGANISM: Alcaligenes faecalis
<220> FEATURE:
<221> NAME/KEY: Unsure
<222> LOCATION: 1 ... 20
<223> OTHER INFORMATION: n represents g, a, t or c

<400> SEQUENCE: 7
tngcsacnga ngcratcttg                                           20

<210> SEQ ID NO 8
<211> LENGTH: 31
<212> TYPE: DNA
<213> ORGANISM: Alcaligenes faecalis

<400> SEQUENCE: 8
ttaatcatat gcagacaaga aaaatcgtcc g                               31
```

```
<210> SEQ ID NO 9
<211> LENGTH: 32
<212> TYPE: DNA
<213> ORGANISM: Alcaligenes faecalis

<400> SEQUENCE: 9
aaggatcctc aagacggctc ttgcactagc ag                                32
```